US012636093B2

(12) United States Patent
    Kostrzewski et al.

(10) Patent No.: US 12,636,093 B2
(45) Date of Patent: May 26, 2026

(54) ROBOTIC SYSTEM AND METHOD FOR SPINAL AND OTHER SURGERIES

(71) Applicant: KB Medical SA, Audubon, PA (US)

(72) Inventors: Szymon Kostrzewski, Lausanne (CH); Philippe Berard, Chavannes-pres-Renens (CH); Charles Baur, Saint-Aubin-Sauges (CH); John Michael Duff, La Croix-sur-Lutry (CH); Kishore Sandu, Savigny (CH)

(73) Assignee: KB Medical SA, Audubon, PA (US)

( * ) Notice: Subject to any disclaimer, the term of this patent is extended or adjusted under 35 U.S.C. 154(b) by 105 days.

(21) Appl. No.: 18/813,656

(22) Filed: Aug. 23, 2024

(65) Prior Publication Data

US 2024/0415582 A1      Dec. 19, 2024

Related U.S. Application Data

(63) Continuation of application No. 17/514,181, filed on Oct. 29, 2021, now Pat. No. 12,096,994, which is a
(Continued)

(51) Int. Cl.
    *A61B 34/20*      (2016.01)
    *A61B 5/11*       (2006.01)
    (Continued)

(52) U.S. Cl.
    CPC ............ *A61B 34/20* (2016.02); *A61B 5/1127* (2013.01); *A61B 17/1671* (2013.01); *A61B 17/1703* (2013.01); *A61B 17/7082* (2013.01); *A61B 17/86* (2013.01); *A61B 34/25* (2016.02); *A61B 34/30* (2016.02); *A61B 34/76* (2016.02);

*A61B 90/06* (2016.02); *A61B 90/50* (2016.02); *A61B 90/57* (2016.02); *A61B 2017/00694* (2013.01); *A61B 2034/107* (2016.02);
(Continued)

(58) Field of Classification Search
    CPC .......... A61B 34/20–2034/306; A61B 19/2203; A61B 19/5244
    See application file for complete search history.

(56) References Cited

U.S. PATENT DOCUMENTS 4,150,293 A    4/1979    Franke
5,246,010 A    9/1993    Gazzara et al.
               (Continued)

FOREIGN PATENT DOCUMENTS

WO    WO-2005122916 A1 *  12/2005    ........... A61B 17/154
WO    WO-2007136768 A2 *  11/2007    ............. A61B 90/03
WO    WO-2008097540 A2 *  8/2008     ............. A61B 34/71

OTHER PUBLICATIONS

US 8,231,638 B2, 07/2012, Swarup et al. (withdrawn)

*Primary Examiner* — Zade Coley

(57)                ABSTRACT

The present invention relates to a method, such as a surgical method for assisting a surgeon for placing screws in the spine using a robot attached to a passive structure. The present invention also related to a method, such as a surgical method for assisting a surgeon for removing volumes in the body of a patient using a robot attached to a passive structure and to a device to carry out said methods. The present invention further concerns a device suitable to carry out the methods according to the present invention.

20 Claims, 8 Drawing Sheets

Related U.S. Application Data continuation of application No. 15/783,051, filed on Oct. 13, 2017, now Pat. No. 11,202,681, which is a continuation of application No. 15/705,578, filed on Sep. 15, 2017, now Pat. No. 10,660,712, which is a continuation of application No. 14/824,602, filed on Aug. 12, 2015, now Pat. No. 9,833,292, which is a continuation of application No. 14/522,509, filed on Oct. 23, 2014, now Pat. No. 9,125,680, which is a continuation of application No. 14/009,050, filed as application No. PCT/IB2012/051611 on Apr. 2, 2012, now Pat. No. 9,308,050.

(60) Provisional application No. 61/470,545, filed on Apr. 1, 2011.

(51) Int. Cl.

| | |
|---|---|
| *A61B 17/16* | (2006.01) |
| *A61B 17/17* | (2006.01) |
| *A61B 17/70* | (2006.01) |
| *A61B 17/86* | (2006.01) |
| *A61B 34/00* | (2016.01) |
| *A61B 34/30* | (2016.01) |
| *A61B 90/00* | (2016.01) |
| *A61B 90/50* | (2016.01) |
| *A61B 90/57* | (2016.01) |
| *A61B 17/00* | (2006.01) |
| *A61B 34/10* | (2016.01) |
| *A61B 90/90* | (2016.01) |

(52) U.S. Cl.
CPC . *A61B 2034/2057* (2016.02); *A61B 2034/301* (2016.02); *A61B 2034/302* (2016.02); *A61B 2034/303* (2016.02); *A61B 2034/305* (2016.02); *A61B 2090/061* (2016.02); *A61B 2090/062* (2016.02); *A61B 2090/064* (2016.02); *A61B 2090/067* (2016.02); *A61B 2090/3937* (2016.02); *A61B 2090/3983* (2016.02); *A61B 90/90* (2016.02); *Y10S 901/03* (2013.01); *Y10S 901/09* (2013.01)

(56) References Cited

U.S. PATENT DOCUMENTS

| | | | |
|---|---|---|---|
| 5,354,314 A | | 10/1994 | Hardy et al. |
| 5,397,323 A | | 3/1995 | Taylor et al. |
| 5,408,409 A | * | 4/1995 | Glassman .......... G05B 19/4099 |
| | | | 600/407 |
| 5,598,453 A | | 1/1997 | Baba et al. |
| 5,772,594 A | | 6/1998 | Barrick |
| 5,791,908 A | | 8/1998 | Gillio |
| 5,820,559 A | | 10/1998 | Ng et al. |
| 5,825,982 A | | 10/1998 | Wright et al. |
| 5,887,121 A | | 3/1999 | Funda et al. |
| 5,911,449 A | | 6/1999 | Daniele et al. |
| 5,951,475 A | | 9/1999 | Gueziec et al. |
| 5,987,960 A | | 11/1999 | Messner et al. |
| 6,012,216 A | | 1/2000 | Esteves et al. |
| 6,031,888 A | | 2/2000 | Ivan et al. |
| 6,033,415 A | | 3/2000 | Mittelstadt et al. |
| 6,080,181 A | | 6/2000 | Jensen et al. |
| 6,106,511 A | | 8/2000 | Jensen |
| 6,122,541 A | | 9/2000 | Cosman et al. |
| 6,144,875 A | | 11/2000 | Schweikard et al. |
| 6,157,853 A | | 12/2000 | Blume et al. |
| 6,167,145 A | | 12/2000 | Foley et al. |
| 6,167,292 A | | 12/2000 | Badano et al. |
| 6,201,984 B1 | | 3/2001 | Funda et al. |
| 6,203,196 B1 | | 3/2001 | Meyer et al. |
| 6,205,411 B1 | | 3/2001 | DiGioia, III et al. |
| 6,212,419 B1 | | 4/2001 | Blume et al. |
| 6,231,565 B1 | | 5/2001 | Tovey et al. |
| 6,236,875 B1 | | 5/2001 | Bucholz et al. |
| 6,246,900 B1 | | 6/2001 | Cosman et al. |
| 6,301,495 B1 | | 10/2001 | Gueziec et al. |
| 6,306,126 B1 | | 10/2001 | Montezuma |
| 6,312,435 B1 | | 11/2001 | Wallace et al. |
| 6,314,311 B1 | | 11/2001 | Williams et al. |
| 6,320,929 B1 | | 11/2001 | Von Der Haar |
| 6,322,567 B1 | | 11/2001 | Mittelstadt et al. |
| 6,325,808 B1 | | 12/2001 | Bernard et al. |
| 6,340,363 B1 | | 1/2002 | Bolger et al. |
| 6,377,011 B1 | | 4/2002 | Ben-Ur |
| 6,379,302 B1 | | 4/2002 | Kessman et al. |
| 6,402,762 B2 | | 6/2002 | Hunter et al. |
| 6,424,885 B1 | | 7/2002 | Niemeyer et al. |
| 6,447,503 B1 | | 9/2002 | Wynne et al. |
| 6,451,027 B1 | | 9/2002 | Cooper et al. |
| 6,477,400 B1 | | 11/2002 | Barrick |
| 6,484,049 B1 | | 11/2002 | Seeley et al. |
| 6,487,267 B1 | | 11/2002 | Wolter |
| 6,490,467 B1 | | 12/2002 | Bucholz et al. |
| 6,490,475 B1 | | 12/2002 | Seeley et al. |
| 6,499,488 B1 | | 12/2002 | Hunter et al. |
| 6,501,981 B1 | | 12/2002 | Schweikard et al. |
| 6,507,751 B2 | | 1/2003 | Blume et al. |
| 6,535,756 B1 | | 3/2003 | Simon et al. |
| 6,560,354 B1 | | 5/2003 | Maurer, Jr. et al. |
| 6,565,554 B1 | | 5/2003 | Niemeyer |
| 6,587,750 B2 | | 7/2003 | Gerbi et al. |
| 6,614,453 B1 | | 9/2003 | Suri et al. |
| 6,614,871 B1 | | 9/2003 | Kobiki et al. |
| 6,619,840 B2 | | 9/2003 | Rasche et al. |
| 6,636,757 B1 | | 10/2003 | Jascob et al. |
| 6,645,196 B1 | | 11/2003 | Nixon et al. |
| 6,666,579 B2 | | 12/2003 | Jensen |
| 6,669,635 B2 | | 12/2003 | Kessman et al. |
| 6,701,173 B2 | | 3/2004 | Nowinski et al. |
| 6,757,068 B2 | | 6/2004 | Foxlin |
| 6,782,287 B2 | | 8/2004 | Grzeszczuk et al. |
| 6,783,524 B2 | | 8/2004 | Anderson et al. |
| 6,786,896 B1 | | 9/2004 | Madhani et al. |
| 6,788,018 B1 | | 9/2004 | Blumenkranz |
| 6,804,581 B2 | | 10/2004 | Wang et al. |
| 6,823,207 B1 | | 11/2004 | Jensen et al. |
| 6,827,351 B2 | | 12/2004 | Graziani et al. |
| 6,837,892 B2 | | 1/2005 | Shoham |
| 6,839,612 B2 | | 1/2005 | Sanchez et al. |
| 6,856,826 B2 | | 2/2005 | Seeley et al. |
| 6,856,827 B2 | | 2/2005 | Seeley et al. |
| 6,879,880 B2 | | 4/2005 | Nowlin et al. |
| 6,892,090 B2 | | 5/2005 | Verard et al. |
| 6,920,347 B2 | | 7/2005 | Simon et al. |
| 6,922,632 B2 | | 7/2005 | Foxlin |
| 6,968,224 B2 | | 11/2005 | Kessman et al. |
| 6,978,166 B2 | | 12/2005 | Foley et al. |
| 6,988,009 B2 | | 1/2006 | Grimm et al. |
| 6,991,627 B2 | | 1/2006 | Madhani et al. |
| 6,996,487 B2 | | 2/2006 | Jutras et al. |
| 6,999,852 B2 | | 2/2006 | Green |
| 7,007,699 B2 | | 3/2006 | Martinelli et al. |
| 7,016,457 B1 | | 3/2006 | Senzig et al. |
| 7,043,961 B2 | | 5/2006 | Pandey et al. |
| 7,062,006 B1 | | 6/2006 | Pelc et al. |
| 7,063,705 B2 | | 6/2006 | Young et al. |
| 7,072,707 B2 | | 7/2006 | Galloway, Jr. et al. |
| 7,083,615 B2 | | 8/2006 | Peterson et al. |
| 7,097,640 B2 | | 8/2006 | Wang et al. |
| 7,099,428 B2 | | 8/2006 | Clinthorne et al. |
| 7,108,421 B2 | | 9/2006 | Gregerson et al. |
| 7,130,676 B2 | | 10/2006 | Barrick |
| 7,139,418 B2 | | 11/2006 | Abovitz et al. |
| 7,139,601 B2 | | 11/2006 | Bucholz et al. |
| 7,155,316 B2 | * | 12/2006 | Sutherland ............. A61B 34/37 |
| | | | 901/1 |
| 7,164,968 B2 | | 1/2007 | Treat et al. |
| 7,167,738 B2 | | 1/2007 | Schweikard et al. |
| 7,169,141 B2 | | 1/2007 | Brock et al. |
| 7,172,627 B2 | | 2/2007 | Fiere et al. |

(56) References Cited

U.S. PATENT DOCUMENTS

| | | | |
|---|---|---|---|
| 7,194,120 | B2 | 3/2007 | Wicker et al. |
| 7,196,454 | B2 * | 3/2007 | Baur ..................... H02N 2/101 |
| | | | 310/323.03 |
| 7,197,107 | B2 | 3/2007 | Arai et al. |
| 7,231,014 | B2 | 6/2007 | Levy |
| 7,231,063 | B2 | 6/2007 | Naimark et al. |
| 7,239,940 | B2 | 7/2007 | Wang et al. |
| 7,248,914 | B2 | 7/2007 | Hastings et al. |
| 7,301,648 | B2 | 11/2007 | Foxlin |
| 7,302,288 | B1 | 11/2007 | Schellenberg |
| 7,313,430 | B2 | 12/2007 | Urquhart et al. |
| 7,318,805 | B2 | 1/2008 | Schweikard et al. |
| 7,318,827 | B2 | 1/2008 | Leitner et al. |
| 7,319,897 | B2 | 1/2008 | Leitner et al. |
| 7,324,623 | B2 | 1/2008 | Heuscher et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |
| 7,366,562 | B2 | 4/2008 | Dukesherer et al. |
| 7,379,790 | B2 | 5/2008 | Toth et al. |
| 7,386,365 | B2 | 6/2008 | Nixon |
| 7,422,592 | B2 | 9/2008 | Morley et al. |
| 7,435,216 | B2 | 10/2008 | Kwon et al. |
| 7,440,793 | B2 | 10/2008 | Chauhan et al. |
| 7,460,637 | B2 | 12/2008 | Clinthorne et al. |
| 7,466,303 | B2 | 12/2008 | Yi et al. |
| 7,493,153 | B2 | 2/2009 | Ahmed et al. |
| 7,505,617 | B2 | 3/2009 | Fu et al. |
| 7,533,892 | B2 | 5/2009 | Schena et al. |
| 7,542,791 | B2 | 6/2009 | Mire et al. |
| 7,555,331 | B2 | 6/2009 | Viswanathan |
| 7,567,834 | B2 | 7/2009 | Clayton et al. |
| 7,594,912 | B2 | 9/2009 | Cooper et al. |
| 7,606,613 | B2 | 10/2009 | Simon et al. |
| 7,607,440 | B2 | 10/2009 | Coste-Maniere et al. |
| 7,623,902 | B2 | 11/2009 | Pacheco |
| 7,630,752 | B2 | 12/2009 | Viswanathan |
| 7,630,753 | B2 | 12/2009 | Simon et al. |
| 7,643,862 | B2 | 1/2010 | Schoenefeld |
| 7,660,623 | B2 | 2/2010 | Hunter et al. |
| 7,661,881 | B2 | 2/2010 | Gregerson et al. |
| 7,683,331 | B2 | 3/2010 | Chang |
| 7,683,332 | B2 | 3/2010 | Chang |
| 7,689,320 | B2 | 3/2010 | Prisco et al. |
| 7,691,098 | B2 | 4/2010 | Wallace et al. |
| 7,702,379 | B2 | 4/2010 | Avinash et al. |
| 7,702,477 | B2 | 4/2010 | Tuemmler et al. |
| 7,711,083 | B2 | 5/2010 | Heigl et al. |
| 7,711,406 | B2 | 5/2010 | Kuhn et al. |
| 7,720,523 | B2 | 5/2010 | Omernick et al. |
| 7,725,253 | B2 | 5/2010 | Foxlin |
| 7,726,171 | B2 | 6/2010 | Langlotz et al. |
| 7,742,801 | B2 | 6/2010 | Neubauer et al. |
| 7,751,865 | B2 | 7/2010 | Jascob et al. |
| 7,760,849 | B2 | 7/2010 | Zhang |
| 7,762,825 | B2 | 7/2010 | Burbank et al. |
| 7,763,015 | B2 | 7/2010 | Cooper et al. |
| 7,787,699 | B2 | 8/2010 | Mahesh et al. |
| 7,796,728 | B2 | 9/2010 | Bergfjord |
| 7,813,838 | B2 | 10/2010 | Sommer |
| 7,818,044 | B2 | 10/2010 | Dukesherer et al. |
| 7,819,859 | B2 | 10/2010 | Prisco et al. |
| 7,824,401 | B2 | 11/2010 | Manzo et al. |
| 7,831,294 | B2 | 11/2010 | Viswanathan |
| 7,834,484 | B2 | 11/2010 | Sartor |
| 7,835,557 | B2 | 11/2010 | Kendrick et al. |
| 7,835,778 | B2 | 11/2010 | Foley et al. |
| 7,835,784 | B2 | 11/2010 | Mire et al. |
| 7,840,253 | B2 | 11/2010 | Tremblay et al. |
| 7,840,256 | B2 | 11/2010 | Lakin et al. |
| 7,843,158 | B2 | 11/2010 | Prisco |
| 7,844,320 | B2 | 11/2010 | Shahidi |
| 7,853,305 | B2 | 12/2010 | Simon et al. |
| 7,853,313 | B2 | 12/2010 | Thompson |
| 7,865,269 | B2 | 1/2011 | Prisco et al. |
| D631,966 | S | 2/2011 | Perloff et al. |
| 7,879,045 | B2 | 2/2011 | Gielen et al. |
| 7,881,767 | B2 | 2/2011 | Strommer et al. |
| 7,881,770 | B2 | 2/2011 | Melkent et al. |
| 7,886,743 | B2 | 2/2011 | Cooper et al. |
| RE42,194 | E | 3/2011 | Foley et al. |
| RE42,226 | E | 3/2011 | Foley et al. |
| 7,900,524 | B2 | 3/2011 | Calloway et al. |
| 7,907,166 | B2 | 3/2011 | Lamprecht et al. |
| 7,909,122 | B2 | 3/2011 | Schena et al. |
| 7,925,653 | B2 | 4/2011 | Saptharishi |
| 7,930,065 | B2 | 4/2011 | Larkin et al. |
| 7,935,130 | B2 | 5/2011 | Willliams |
| 7,940,999 | B2 | 5/2011 | Liao et al. |
| 7,945,012 | B2 | 5/2011 | Ye et al. |
| 7,945,021 | B2 | 5/2011 | Shapiro et al. |
| 7,953,470 | B2 | 5/2011 | Vetter et al. |
| 7,954,397 | B2 | 6/2011 | Choi et al. |
| 7,971,341 | B2 | 7/2011 | Dukesherer et al. |
| 7,974,674 | B2 | 7/2011 | Hauck et al. |
| 7,974,677 | B2 | 7/2011 | Mire et al. |
| 7,974,681 | B2 | 7/2011 | Wallace et al. |
| 7,979,157 | B2 | 7/2011 | Anvari |
| 7,983,733 | B2 | 7/2011 | Viswanathan |
| 7,988,215 | B2 | 8/2011 | Seibold |
| 7,996,110 | B2 | 8/2011 | Lipow et al. |
| 8,004,121 | B2 | 8/2011 | Sartor |
| 8,004,229 | B2 | 8/2011 | Nowlin et al. |
| 8,010,177 | B2 | 8/2011 | Csavoy et al. |
| 8,019,045 | B2 | 9/2011 | Kato |
| 8,021,310 | B2 | 9/2011 | Sanborn et al. |
| 8,035,685 | B2 | 10/2011 | Jensen |
| 8,046,054 | B2 | 10/2011 | Kim et al. |
| 8,046,057 | B2 | 10/2011 | Clarke |
| 8,052,688 | B2 | 11/2011 | Wolf, II |
| 8,054,184 | B2 | 11/2011 | Cline et al. |
| 8,054,752 | B2 | 11/2011 | Druke et al. |
| 8,057,397 | B2 | 11/2011 | Li et al. |
| 8,057,407 | B2 | 11/2011 | Martinelli et al. |
| 8,062,288 | B2 | 11/2011 | Cooper et al. |
| 8,062,375 | B2 | 11/2011 | Glerum et al. |
| 8,066,524 | B2 | 11/2011 | Burbank et al. |
| 8,073,335 | B2 | 12/2011 | Labonville et al. |
| 8,079,950 | B2 | 12/2011 | Stern et al. |
| 8,086,299 | B2 | 12/2011 | Adler et al. |
| 8,092,370 | B2 | 1/2012 | Roberts et al. |
| 8,098,914 | B2 | 1/2012 | Liao et al. |
| 8,100,950 | B2 | 1/2012 | St. Clair et al. |
| 8,105,320 | B2 | 1/2012 | Manzo |
| 8,108,025 | B2 | 1/2012 | Csavoy et al. |
| 8,109,877 | B2 | 2/2012 | Moctezuma de la Barrera et al. |
| 8,112,292 | B2 | 2/2012 | Simon |
| 8,116,430 | B1 | 2/2012 | Shapiro et al. |
| 8,120,301 | B2 | 2/2012 | Goldberg et al. |
| 8,121,249 | B2 | 2/2012 | Wang et al. |
| 8,123,675 | B2 | 2/2012 | Funda et al. |
| 8,133,229 | B1 | 3/2012 | Bonutti |
| 8,142,420 | B2 | 3/2012 | Schena |
| 8,147,494 | B2 | 4/2012 | Leitner et al. |
| 8,150,494 | B2 | 4/2012 | Simon et al. |
| 8,150,497 | B2 | 4/2012 | Gielen et al. |
| 8,150,498 | B2 | 4/2012 | Gielen et al. |
| 8,165,658 | B2 | 4/2012 | Waynik et al. |
| 8,170,313 | B2 | 5/2012 | Kendrick et al. |
| 8,179,073 | B2 | 5/2012 | Farritor et al. |
| 8,182,476 | B2 | 5/2012 | Julian et al. |
| 8,184,880 | B2 | 5/2012 | Zhao et al. |
| 8,202,278 | B2 | 6/2012 | Orban, III et al. |
| 8,208,708 | B2 | 6/2012 | Homan et al. |
| 8,208,988 | B2 | 6/2012 | Jensen |
| 8,219,177 | B2 | 7/2012 | Smith et al. |
| 8,219,178 | B2 | 7/2012 | Smith et al. |
| 8,220,468 | B2 | 7/2012 | Cooper et al. |
| 8,224,024 | B2 | 7/2012 | Foxlin et al. |
| 8,224,484 | B2 | 7/2012 | Swarup et al. |
| 8,225,798 | B2 | 7/2012 | Baldwin et al. |
| 8,228,368 | B2 | 7/2012 | Zhao et al. |
| 8,231,610 | B2 | 7/2012 | Jo et al. |

(56)  References Cited

U.S. PATENT DOCUMENTS

| | | | |
|---|---|---|---|
| 8,239,001 | B2 | 8/2012 | Verard et al. |
| 8,241,271 | B2 | 8/2012 | Millman et al. |
| 8,248,413 | B2 | 8/2012 | Gattani et al. |
| 8,256,319 | B2 | 9/2012 | Cooper et al. |
| 8,263,933 | B2 | 9/2012 | Zeile |
| 8,271,069 | B2 | 9/2012 | Jascob et al. |
| 8,271,130 | B2 | 9/2012 | Hourtash |
| 8,281,670 | B2 | 10/2012 | Larkin et al. |
| 8,282,653 | B2 | 10/2012 | Nelson et al. |
| 8,301,226 | B2 | 10/2012 | Csavoy et al. |
| 8,311,611 | B2 | 11/2012 | Csavoy et al. |
| 8,320,991 | B2 | 11/2012 | Jascob et al. |
| 8,332,012 | B2 | 12/2012 | Kienzle, III |
| 8,333,755 | B2 | 12/2012 | Cooper et al. |
| 8,335,552 | B2 | 12/2012 | Stiles |
| 8,335,557 | B2 | 12/2012 | Maschke |
| 8,348,931 | B2 | 1/2013 | Cooper et al. |
| 8,353,963 | B2 | 1/2013 | Glerum |
| 8,358,818 | B2 | 1/2013 | Miga et al. |
| 8,359,730 | B2 | 1/2013 | Burg et al. |
| 8,374,673 | B2 | 2/2013 | Adcox et al. |
| 8,374,723 | B2 | 2/2013 | Zhao et al. |
| 8,379,791 | B2 | 2/2013 | Forthmann et al. |
| 8,386,019 | B2 | 2/2013 | Camus et al. |
| 8,392,022 | B2 | 3/2013 | Ortmaier et al. |
| 8,394,099 | B2 | 3/2013 | Patwardhan |
| 8,395,342 | B2 | 3/2013 | Prisco |
| 8,398,634 | B2 | 3/2013 | Manzo et al. |
| 8,400,094 | B2 | 3/2013 | Schena |
| 8,414,957 | B2 | 4/2013 | Enzerink et al. |
| 8,418,073 | B2 | 4/2013 | Mohr et al. |
| 8,450,694 | B2 | 5/2013 | Baviera et al. |
| 8,452,447 | B2 | 5/2013 | Nixon |
| RE44,305 | E | 6/2013 | Foley et al. |
| 8,462,911 | B2 | 6/2013 | Vesel et al. |
| 8,465,476 | B2 | 6/2013 | Rogers et al. |
| 8,465,771 | B2 | 6/2013 | Wan et al. |
| 8,467,851 | B2 | 6/2013 | Mire et al. |
| 8,467,852 | B2 | 6/2013 | Csavoy et al. |
| 8,469,947 | B2 | 6/2013 | Devengenzo et al. |
| RE44,392 | E | 7/2013 | Hynes |
| 8,483,434 | B2 | 7/2013 | Buehner et al. |
| 8,483,800 | B2 | 7/2013 | Jensen et al. |
| 8,486,532 | B2 | 7/2013 | Enzerink et al. |
| 8,489,235 | B2 | 7/2013 | Moll et al. |
| 8,500,722 | B2 | 8/2013 | Cooper |
| 8,500,728 | B2 | 8/2013 | Newton et al. |
| 8,504,201 | B2 | 8/2013 | Moll et al. |
| 8,506,555 | B2 | 8/2013 | Ruiz Morales |
| 8,506,556 | B2 | 8/2013 | Schena |
| 8,508,173 | B2 | 8/2013 | Goldberg et al. |
| 8,512,318 | B2 | 8/2013 | Tovey et al. |
| 8,515,576 | B2 | 8/2013 | Lipow et al. |
| 8,518,120 | B2 | 8/2013 | Glerum et al. |
| 8,521,331 | B2 | 8/2013 | Itkowitz |
| 8,526,688 | B2 | 9/2013 | Groszmann et al. |
| 8,526,700 | B2 | 9/2013 | Issacs |
| 8,527,094 | B2 | 9/2013 | Kumar et al. |
| 8,528,440 | B2 | 9/2013 | Morley et al. |
| 8,532,741 | B2 | 9/2013 | Heruth et al. |
| 8,541,970 | B2 | 9/2013 | Nowlin et al. |
| 8,548,563 | B2 | 10/2013 | Simon et al. |
| 8,549,732 | B2 | 10/2013 | Burg et al. |
| 8,551,114 | B2 | 10/2013 | Ramos de la Pena |
| 8,551,116 | B2 | 10/2013 | Julian et al. |
| 8,556,807 | B2 | 10/2013 | Scott et al. |
| 8,556,979 | B2 | 10/2013 | Glerum et al. |
| 8,560,118 | B2 | 10/2013 | Green et al. |
| 8,561,473 | B2 | 10/2013 | Blumenkranz |
| 8,562,594 | B2 | 10/2013 | Cooper et al. |
| 8,571,638 | B2 | 10/2013 | Shoham |
| 8,571,710 | B2 | 10/2013 | Coste-Maniere et al. |
| 8,573,465 | B2 | 11/2013 | Shelton, IV |
| 8,574,303 | B2 | 11/2013 | Sharkey et al. |
| 8,585,420 | B2 | 11/2013 | Burbank et al. |
| 8,594,841 | B2 | 11/2013 | Zhao et al. |
| 8,597,198 | B2 | 12/2013 | Sanborn et al. |
| 8,600,478 | B2 | 12/2013 | Verard et al. |
| 8,603,077 | B2 | 12/2013 | Cooper et al. |
| 8,611,985 | B2 | 12/2013 | Lavallee et al. |
| 8,613,230 | B2 | 12/2013 | Blumenkranz et al. |
| 8,621,939 | B2 | 1/2014 | Blumenkranz et al. |
| 8,624,537 | B2 | 1/2014 | Nowlin et al. |
| 8,630,389 | B2 | 1/2014 | Kato |
| 8,634,897 | B2 | 1/2014 | Simon et al. |
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,639,000 | B2 | 1/2014 | Zhao et al. |
| 8,641,726 | B2 | 2/2014 | Bonutti |
| 8,644,907 | B2 | 2/2014 | Hartmann et al. |
| 8,657,809 | B2 | 2/2014 | Schoepp |
| 8,660,635 | B2 | 2/2014 | Simon et al. |
| 8,666,544 | B2 | 3/2014 | Moll et al. |
| 8,675,939 | B2 | 3/2014 | Moctezuma de la Barrera |
| 8,678,647 | B2 | 3/2014 | Gregerson et al. |
| 8,679,125 | B2 | 3/2014 | Smith et al. |
| 8,679,183 | B2 | 3/2014 | Glerum et al. |
| 8,682,413 | B2 | 3/2014 | Lloyd |
| 8,684,253 | B2 | 4/2014 | Giordano et al. |
| 8,685,098 | B2 | 4/2014 | Glerum et al. |
| 8,693,730 | B2 | 4/2014 | Umasuthan et al. |
| 8,694,075 | B2 | 4/2014 | Groszmann et al. |
| 8,696,458 | B2 | 4/2014 | Foxlin et al. |
| 8,700,123 | B2 | 4/2014 | Okamura et al. |
| 8,706,086 | B2 | 4/2014 | Glerum |
| 8,706,185 | B2 | 4/2014 | Foley et al. |
| 8,706,301 | B2 | 4/2014 | Zhao et al. |
| 8,717,430 | B2 | 5/2014 | Simon et al. |
| 8,727,618 | B2 | 5/2014 | Maschke et al. |
| 8,734,432 | B2 | 5/2014 | Tuma et al. |
| 8,738,115 | B2 | 5/2014 | Amberg et al. |
| 8,738,181 | B2 | 5/2014 | Greer et al. |
| 8,740,882 | B2 | 6/2014 | Jun et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,761,930 | B2 | 6/2014 | Nixon |
| 8,764,448 | B2 | 7/2014 | Yang et al. |
| 8,771,170 | B2 | 7/2014 | Mesallum et al. |
| 8,781,186 | B2 | 7/2014 | Clements et al. |
| 8,781,630 | B2 | 7/2014 | Banks et al. |
| 8,784,385 | B2 | 7/2014 | Boyden et al. |
| 8,786,241 | B2 | 7/2014 | Nowlin et al. |
| 8,787,520 | B2 | 7/2014 | Baba |
| 8,792,704 | B2 | 7/2014 | Isaacs |
| 8,798,231 | B2 | 8/2014 | Notohara et al. |
| 8,800,838 | B2 | 8/2014 | Shelton, IV |
| 8,808,164 | B2 | 8/2014 | Hoffman et al. |
| 8,812,077 | B2 | 8/2014 | Dempsey |
| 8,814,793 | B2 | 8/2014 | Brabrand |
| 8,816,628 | B2 | 8/2014 | Nowlin et al. |
| 8,818,105 | B2 | 8/2014 | Myronenko et al. |
| 8,820,605 | B2 | 9/2014 | Shelton, IV |
| 8,821,511 | B2 | 9/2014 | von Jako et al. |
| 8,823,308 | B2 | 9/2014 | Nowlin et al. |
| 8,827,996 | B2 | 9/2014 | Scott et al. |
| 8,828,024 | B2 | 9/2014 | Farritor et al. |
| 8,830,224 | B2 | 9/2014 | Zhao et al. |
| 8,834,489 | B2 | 9/2014 | Cooper et al. |
| 8,834,490 | B2 | 9/2014 | Bonutti |
| 8,838,270 | B2 | 9/2014 | Druke et al. |
| 8,844,789 | B2 | 9/2014 | Shelton, IV et al. |
| 8,855,822 | B2 | 10/2014 | Bartol et al. |
| 8,858,598 | B2 | 10/2014 | Seifert et al. |
| 8,860,753 | B2 | 10/2014 | Bhandarkar et al. |
| 8,864,751 | B2 | 10/2014 | Prisco et al. |
| 8,864,798 | B2 | 10/2014 | Weiman et al. |
| 8,864,833 | B2 | 10/2014 | Glerum et al. |
| 8,867,703 | B2 | 10/2014 | Shapiro et al. |
| 8,870,880 | B2 | 10/2014 | Himmelberger et al. |
| 8,876,866 | B2 | 11/2014 | Zappacosta et al. |
| 8,880,223 | B2 | 11/2014 | Raj et al. |
| 8,882,803 | B2 | 11/2014 | Iott et al. |

(56) References Cited

U.S. PATENT DOCUMENTS

| | | | |
|---|---|---|---|
| 8,883,210 B1 | 11/2014 | Truncale et al. | |
| 8,888,821 B2 | 11/2014 | Rezach et al. | |
| 8,888,853 B2 | 11/2014 | Glerum et al. | |
| 8,888,854 B2 | 11/2014 | Glerum et al. | |
| 8,894,652 B2 | 11/2014 | Seifert et al. | |
| 8,894,688 B2 | 11/2014 | Suh | |
| 8,894,691 B2 | 11/2014 | Iott et al. | |
| 8,906,069 B2 | 12/2014 | Hansell et al. | |
| 8,964,934 B2 | 2/2015 | Ein-Gal | |
| 8,992,580 B2 | 3/2015 | Bar et al. | |
| 8,996,169 B2 | 3/2015 | Lightcap et al. | |
| 9,001,963 B2 | 4/2015 | Sowards-Emmerd et al. | |
| 9,002,076 B2 | 4/2015 | Khadem et al. | |
| 9,044,190 B2 | 6/2015 | Rubner et al. | |
| 9,107,683 B2 | 8/2015 | Hourtash et al. | |
| 9,125,556 B2 | 9/2015 | Zehavi et al. | |
| 9,131,986 B2 | 9/2015 | Greer et al. | |
| 9,215,968 B2 | 12/2015 | Schostek et al. | |
| 9,308,050 B2 | 4/2016 | Kostrzewski et al. | |
| 9,380,984 B2 | 7/2016 | Li et al. | |
| 9,393,039 B2 | 7/2016 | Lechner et al. | |
| 9,398,886 B2 | 7/2016 | Gregerson et al. | |
| 9,398,890 B2 | 7/2016 | Dong et al. | |
| 9,414,859 B2 | 8/2016 | Ballard et al. | |
| 9,420,975 B2 | 8/2016 | Gutfleisch et al. | |
| 9,492,235 B2 | 11/2016 | Hourtash et al. | |
| 9,592,096 B2 | 3/2017 | Maillet et al. | |
| 9,750,465 B2 | 9/2017 | Engel et al. | |
| 9,757,203 B2 | 9/2017 | Hourtash et al. | |
| 9,795,354 B2 | 10/2017 | Menegaz et al. | |
| 9,814,535 B2 | 11/2017 | Bar et al. | |
| 9,820,783 B2 | 11/2017 | Donner et al. | |
| 9,833,265 B2 | 12/2017 | Donner et al. | |
| 9,848,922 B2 | 12/2017 | Tohmeh et al. | |
| 9,925,011 B2 | 3/2018 | Gombert et al. | |
| 9,931,025 B1 | 4/2018 | Graetzel et al. | |
| 10,034,717 B2 | 7/2018 | Miller et al. | |
| 2001/0036302 A1 | 11/2001 | Miller | |
| 2002/0035321 A1 | 3/2002 | Bucholz et al. | |
| 2004/0068172 A1 | 4/2004 | Nowinski et al. | |
| 2004/0076259 A1 | 4/2004 | Jensen et al. | |
| 2005/0096502 A1 | 5/2005 | Khalili | |
| 2005/0143651 A1 | 6/2005 | Verard et al. | |
| 2005/0171558 A1 | 8/2005 | Abovitz et al. | |
| 2006/0100610 A1 | 5/2006 | Wallace et al. | |
| 2006/0142657 A1* | 6/2006 | Quaid | A61B 90/37 |
| | | | 600/424 |
| 2006/0161136 A1* | 7/2006 | Anderson | A61B 34/37 |
| | | | 606/1 |
| 2006/0173329 A1 | 8/2006 | Marquart et al. | |
| 2006/0184396 A1 | 8/2006 | Dennis et al. | |
| 2006/0241416 A1 | 10/2006 | Marquart et al. | |
| 2006/0291612 A1 | 12/2006 | Nishide et al. | |
| 2007/0015987 A1 | 1/2007 | Benlloch Baviera et al. | |
| 2007/0021738 A1 | 1/2007 | Hasser et al. | |
| 2007/0032906 A1* | 2/2007 | Sutherland | A61B 34/71 |
| | | | 700/248 |
| 2007/0038059 A1 | 2/2007 | Sheffer et al. | |
| 2007/0073133 A1 | 3/2007 | Schoenefeld | |
| 2007/0156121 A1 | 7/2007 | Millman et al. | |
| 2007/0156157 A1* | 7/2007 | Nahum | A61B 34/76 |
| | | | 606/130 |
| 2007/0167712 A1 | 7/2007 | Keglovich et al. | |
| 2007/0233238 A1 | 10/2007 | Huynh et al. | |
| 2007/0270685 A1* | 11/2007 | Kang | A61B 90/03 |
| | | | 600/424 |
| 2008/0004523 A1 | 1/2008 | Jensen | |
| 2008/0013809 A1 | 1/2008 | Zhu et al. | |
| 2008/0033283 A1 | 2/2008 | Dellaca et al. | |
| 2008/0046122 A1 | 2/2008 | Manzo et al. | |
| 2008/0082109 A1 | 4/2008 | Moll et al. | |
| 2008/0108912 A1 | 5/2008 | Node-Langlois | |
| 2008/0108991 A1 | 5/2008 | von Jako | |
| 2008/0109012 A1 | 5/2008 | Falco et al. | |
| 2008/0144906 A1 | 6/2008 | Allred et al. | |
| 2008/0161680 A1 | 7/2008 | von Jako et al. | |
| 2008/0161682 A1 | 7/2008 | Kendrick et al. | |
| 2008/0177203 A1 | 7/2008 | von Jako | |
| 2008/0214922 A1 | 9/2008 | Hartmann et al. | |
| 2008/0228068 A1 | 9/2008 | Viswanathan et al. | |
| 2008/0228196 A1 | 9/2008 | Wang et al. | |
| 2008/0235052 A1 | 9/2008 | Node-Langlois et al. | |
| 2008/0269596 A1 | 10/2008 | Revie et al. | |
| 2008/0287771 A1 | 11/2008 | Anderson | |
| 2008/0287781 A1 | 11/2008 | Revie et al. | |
| 2008/0300477 A1 | 12/2008 | Lloyd et al. | |
| 2008/0300478 A1 | 12/2008 | Zuhars et al. | |
| 2008/0302950 A1 | 12/2008 | Park et al. | |
| 2008/0306490 A1 | 12/2008 | Lakin et al. | |
| 2008/0319311 A1 | 12/2008 | Hamadeh | |
| 2009/0012509 A1 | 1/2009 | Csavoy et al. | |
| 2009/0030428 A1 | 1/2009 | Omori et al. | |
| 2009/0080737 A1 | 3/2009 | Battle et al. | |
| 2009/0185655 A1 | 7/2009 | Koken et al. | |
| 2009/0198121 A1 | 8/2009 | Hoheisel | |
| 2009/0216113 A1 | 8/2009 | Meier et al. | |
| 2009/0228019 A1 | 9/2009 | Gross et al. | |
| 2009/0259123 A1 | 10/2009 | Navab et al. | |
| 2009/0259230 A1 | 10/2009 | Khadem et al. | |
| 2009/0264899 A1 | 10/2009 | Appenrodt et al. | |
| 2009/0281417 A1 | 11/2009 | Hartmann et al. | |
| 2009/0326318 A1* | 12/2009 | Tognaccini | A61B 34/37 |
| | | | 600/109 |
| 2010/0022874 A1 | 1/2010 | Wang et al. | |
| 2010/0039506 A1 | 2/2010 | Sarvestani et al. | |
| 2010/0125286 A1 | 5/2010 | Wang et al. | |
| 2010/0130986 A1 | 5/2010 | Mailloux et al. | |
| 2010/0192720 A1* | 8/2010 | Helmer | B25J 9/0015 |
| | | | 901/29 |
| 2010/0228117 A1 | 9/2010 | Hartmann | |
| 2010/0228265 A1 | 9/2010 | Prisco | |
| 2010/0249571 A1 | 9/2010 | Jensen et al. | |
| 2010/0274120 A1 | 10/2010 | Heuscher | |
| 2010/0280363 A1 | 11/2010 | Skarda et al. | |
| 2010/0331858 A1 | 12/2010 | Simaan et al. | |
| 2011/0022229 A1 | 1/2011 | Jang et al. | |
| 2011/0077504 A1 | 3/2011 | Fischer et al. | |
| 2011/0098553 A1 | 4/2011 | Robbins et al. | |
| 2011/0137152 A1 | 6/2011 | Li | |
| 2011/0190789 A1* | 8/2011 | Thiran | A61B 90/11 |
| | | | 606/130 |
| 2011/0213384 A1 | 9/2011 | Jeong | |
| 2011/0224684 A1 | 9/2011 | Larkin et al. | |
| 2011/0224685 A1 | 9/2011 | Larkin et al. | |
| 2011/0224686 A1 | 9/2011 | Larkin et al. | |
| 2011/0224687 A1 | 9/2011 | Larkin et al. | |
| 2011/0224688 A1 | 9/2011 | Larkin et al. | |
| 2011/0224689 A1 | 9/2011 | Larkin et al. | |
| 2011/0224825 A1 | 9/2011 | Larkin et al. | |
| 2011/0230967 A1 | 9/2011 | O'Halloran et al. | |
| 2011/0238080 A1 | 9/2011 | Ranjit et al. | |
| 2011/0276058 A1 | 11/2011 | Choi et al. | |
| 2011/0282189 A1 | 11/2011 | Graumann | |
| 2011/0286573 A1 | 11/2011 | Schretter et al. | |
| 2011/0295062 A1 | 12/2011 | Gratacos Solsona et al. | |
| 2011/0295370 A1 | 12/2011 | Suh et al. | |
| 2011/0306986 A1 | 12/2011 | Lee et al. | |
| 2012/0035507 A1 | 2/2012 | George et al. | |
| 2012/0046668 A1 | 2/2012 | Gantes | |
| 2012/0051498 A1 | 3/2012 | Koishi | |
| 2012/0053597 A1 | 3/2012 | Anvari et al. | |
| 2012/0059248 A1 | 3/2012 | Holsing et al. | |
| 2012/0059378 A1* | 3/2012 | Farrell | A61B 90/25 |
| | | | 606/80 |
| 2012/0071753 A1 | 3/2012 | Hunter et al. | |
| 2012/0108954 A1 | 5/2012 | Schulhauser et al. | |
| 2012/0136372 A1 | 5/2012 | Amat Girbau et al. | |
| 2012/0143084 A1 | 6/2012 | Shoham | |
| 2012/0184839 A1 | 7/2012 | Woerlein | |
| 2012/0197182 A1 | 8/2012 | Millman et al. | |
| 2012/0226145 A1 | 9/2012 | Chang et al. | |
| 2012/0235909 A1 | 9/2012 | Birkenbach et al. | |
| 2012/0245596 A1 | 9/2012 | Meenink | |

(56)                 References Cited

U.S. PATENT DOCUMENTS

| | | |
|---|---|---|
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0130810 A1 | 5/2014 | Azizian et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

* cited by examiner

2

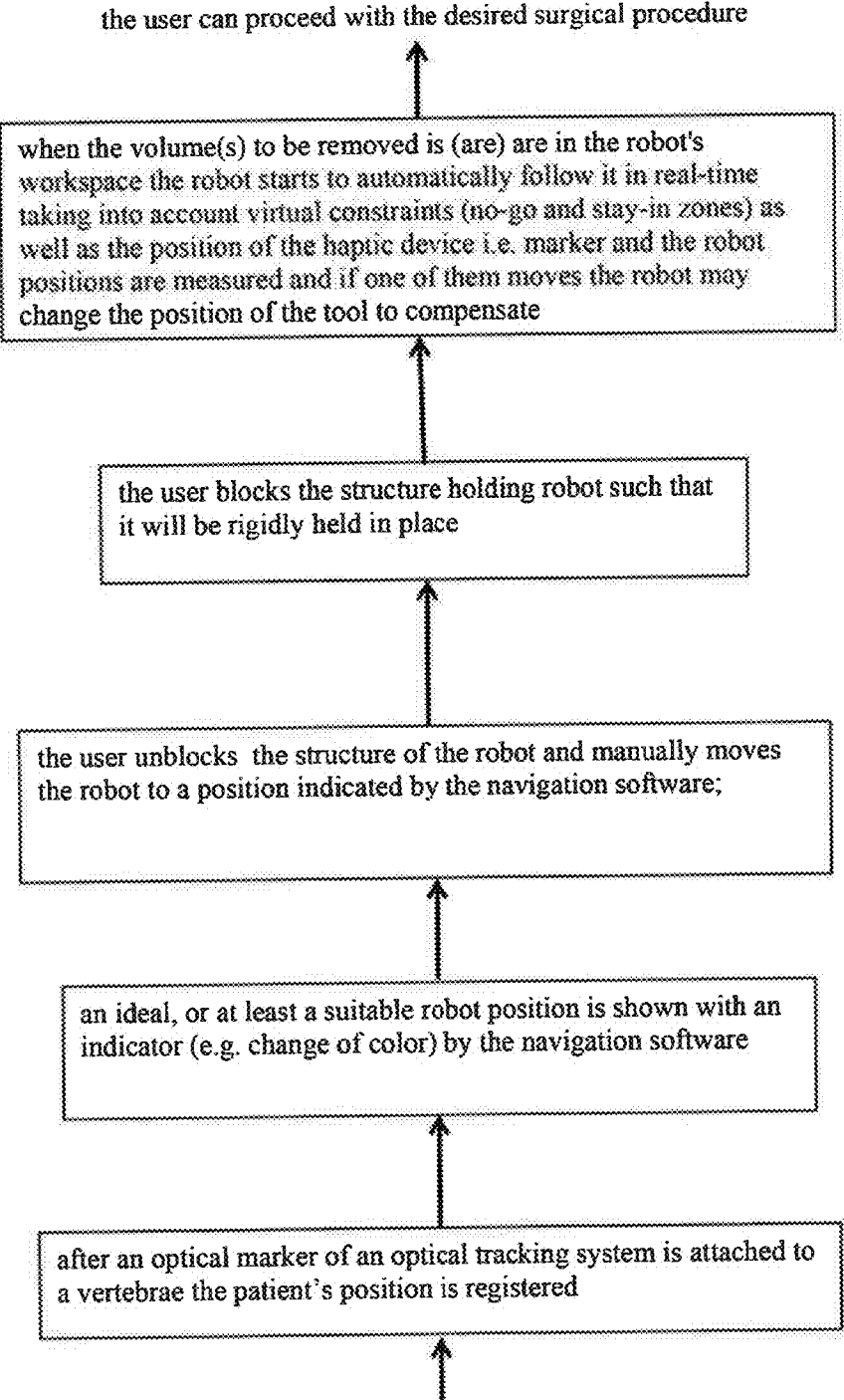

the user can proceed with the desired surgical procedure when the volume(s) to be removed is (are) are in the robot's workspace the robot starts to automatically follow it in real-time taking into account virtual constraints (no-go and stay-in zones) as well as the position of the haptic device i.e. marker and the robot positions are measured and if one of them moves the robot may change the position of the tool to compensate the user blocks the structure holding robot such that it will be rigidly held in place the user unblocks the structure of the robot and manually moves the robot to a position indicated by the navigation software;

an ideal, or at least a suitable robot position is shown with an indicator (e.g. change of color) by the navigation software after an optical marker of an optical tracking system is attached to a vertebrae the patient's position is registered

Figure 6

ROBOTIC SYSTEM AND METHOD FOR SPINAL AND OTHER SURGERIES

CROSS REFERENCE TO RELATED APPLICATIONS

The present application is a continuation of U.S. patent application Ser. No. 17/514,181 filed on Oct. 29, 2021 (published as U.S. Patent Publication No. 2022-0047337), which is a continuation of U.S. patent application Ser. No. 15/783,051 filed on Oct. 13, 2017 (published as U.S. Patent Publication No. 2018-0042684), which is a continuation of U.S. patent application Ser. No. 15/705,578 filed on Sep. 15, 2017, now U.S. Pat. No. 10,660,712, which is a continuation of U.S. patent application Ser. No. 14/824,602 filed on Aug. 12, 2015, now U.S. Pat. No. 9,833,292, which is a continuation of U.S. patent application Ser. No. 14/522,509 filed on Oct. 23, 2014, now U.S. Pat. No. 9,125,680, which is a continuation of U.S. patent application Ser. No. 14/009,050 filed on Jan. 10, 2014, now U.S. Pat. No. 9,308,050, which claims priority to PCT/IB2012/051611, filed Apr. 2, 2012, which claims priority to U.S. Provisional Application 61/470,545 filed on Apr. 1, 2011, the contents of all of which are incorporated by reference herein in their entirety.

FIELD OF THE INVENTION

The present invention concerns a robotic system and methods for surgical procedures. More specifically, the present invention concerns methods for assisting the surgeon to carry out a surgical procedure using a robotic system and computer means.

BACKGROUND OF THE INVENTION

Spine Surgeries

BACKGROUND

Spine surgeries often use fixations and implants attached to vertebrae using screws. It is important to place the screws properly so they do not touch or violate neither spinal cord nor arteries. It can be a difficult task due to the needed precision, high density and constrained access to the vertebrae. For these reasons surgeons use support systems that can enhance the accuracy of the screw placement.

In spine surgeries there are the following methods used for placing the screws:

1. Purely manual
2. Manual using navigation systems
3. Using robotic systems

Manual Methods

In the traditional manual technique, a surgeon on the basis of the pre-operative CT scans visually judges the screw trajectory. During drilling, the fluoroscopic images are taken to verify if the trajectory is correct. An advantage of this technique is that except standard reconstruction systems no additional tools are needed and it can be always used in case of an emergency. On the other hand it strongly relies on the surgeon's experience and can be subject to his changing predisposition. Security is also doubtful as the fluoroscopic images are taken only after the drilling is done. The accuracy and information shown on those images can also vary. Drilling is technically difficult because the tools are held in hand. Surgeon needs to have a very good coordination and be able to simultaneously do many tasks. Due to those disadvantages a screw misplacement rate on the level of 30-50% in the cervical spine was reported.

Manual Methods Using Navigation Systems

Navigation systems can measure the position of surgical tools and a patient in the operating room. Currently most often the optical tracking is used for measurements but other methods such as electro-magnetic tracking can be used. Procedures involving those systems will be referred as the image-guided surgeries. Because of the improved accuracy image-guided procedures made the screw placement in the cervical spine possible for certain patients. The image-guided surgeries in the spinal domain are still done manually. For this reason the surgical tools though tracked can be wrongly positioned because of the human constraints. Precision can be a subject of a variable human factor. These techniques demand increased attention from the surgeon as he needs to coordinate operations with virtual indications on the screen. In case of a procedural error big inaccuracies can appear and for this reason a staff training is important. Problems with the verification of the registration accuracy are common.

Methods Using Robotic Systems

Few attempts have been done to introduce robotic systems for spinal surgeries. One of them is developed at the German Aerospace Center (DLR) Miro/KineMedic robotic system. It is designed for a surgical telemanipulation. The robotic part of the system consists of three lightweight robotic arms. Each joint is equipped with a force sensor and uses a sophisticated control system with the force feedback and the gravity compensation. The robot's redundancy is used for the workspace optimization and allows to fulfill additional criterias in the operating room. Proposition of the possible setup for a pedicle screw placement with the Miro/Kine-Medic system would consist of the DLR lightweight robotic arm, an optical tracking system and the software. The surgeon plans the surgery in advance. In the operating room several robot control modes are available. Initially the robotic arm is moved to the planned position by the surgeon using a hands-on impedance control. When it is in place, the surgeon can start drilling using a driller held by a passive tool holder attached to the robot's end effector. The robot compensates for the position errors while surgeon does axial movement. Authors do not specify in which parts of a spine the robot could work. The proposed registration method using a surface matching only could be insufficient in a general situation as those algorithms need a good starting point and converge to the closest local minimum. It is not specified if in this system standard surgical reconstruction tools could be used which can be crucial for the acceptance in the medical domain. A relatively big robotic arm can have disadvantages in a dense environment of an operating room. It is not said how it would be interfaced with the equipment of an operating room. Sophisticated impedance-control algorithms can be difficult to certify in the medical domain and till now no such arm was certified. Expected accuracy of the system is not mentioned. Accordingly to the author's knowledge no further publications concerning this proposition are available.

Other robotic system for the spinal surgery is the Mazor's SmartAssist. It consists of a miniature robot attached to the spine with a base platform and a workstation for planning and navigation. Registration is based on the matching between pre-operative CT scans and intra-operative fluoroscopic images acquired with a calibrated device. In the next step the robot moves to planned spacial position and the surgeon performs a surgery via the tool guide. The robot does not move during the intervention acting as a tool holder (passive guidance). The system was tested with good results. The SpineAssist can be used only in the thoracic and lumbar parts and can not be used in the cervical spine where high accuracy is most important. Fluoroscopic registration has certain disadvantages and needs a calibrated C-Arm. Possible hard to detect errors were reported. The robotic arm does not compensate for random vertebral movements while drilling. Drill slippage on the surface of the vertebrae causing big inaccuracies was reported.

Another robotic system for spinal surgery is the Cooperative Robotic Assistant. It consists of a 6 degree of freedom robot with a kinematically closed structure. It uses a new drill-by-wire mechanism for placing the screws and uses a 1 degree of freedom haptic device to provide the force feedback for the surgeon. Achieved accuracy below 1 [.mu.m] of the robotic part was reported. Authors claim that closed construction was chosen for rigidity reasons. The robot is taking a lot of space in the operating room. Equipment of the operating room should be strongly adapted to be used with this system. The drill-by-wire mechanism needs its own tools which can be a limit for acceptance in the medical field. The system does not perform any external measurements so nothing about registration methods is known. The precision of the registration will strongly influence the accuracy of the robotic arm measured separately.

Other robotic system is the Spinebot system for the lumbar spine surgery. It consists of a 3 degree of freedom positioner, gimbals and drilling tool having 2 degree of freedom each. It uses an optical tracking system for registration and measurements. Big advantage of the system is that during the surgery holes in spine can be drilled percutaneusly (through the skin). The system can work only in lumbar part of the spine. In this area needed accuracy is much lower than in cervical part and access is easier.

SUMMARY OF THE INVENTION

An aim of the present invention is to improve the known systems and methods.

The invention will be described in more detail in the following specification and with reference to the drawings which show:

FIG. 1 illustrates the different elements of a proposed robotic system for spinal surgeries;

FIGS. 2(*a*) and 2(*b*) illustrate an example of patient registration;

FIGS. 3(*a*) and 3(*b*) illustrate the indicators helping the surgeon to position the robot;

FIG. 6 illustrates a block diagram of the method in another embodiment;

Figure 1:
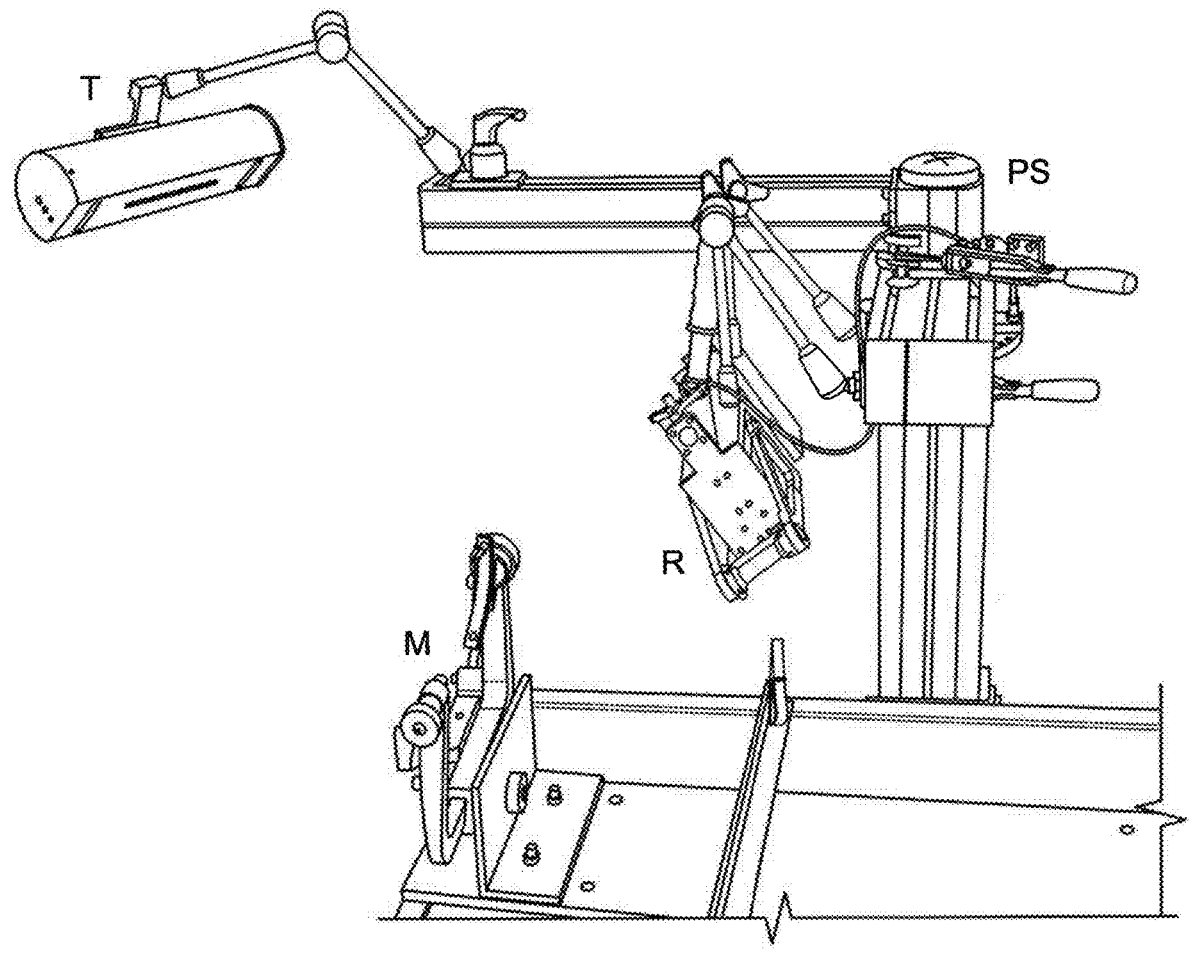

In an embodiment the invention concerns a method for assisting a user for placing screws in the spine of a patient using a robot attached to a passive structure and holding a tool, wherein said method comprises the following steps:

after an marker of an tracking system is attached to a vertebrae the patient's position is registered in that the transformation between the position of the vertebrae and of the attached marker and/or planning is found the robot is positioned such that the planned screw trajectory is inside the robot's workspace by moving the passive structure;

a navigation software assists the user in doing this task, whereby the user unblocks structure of the robot and manually moves the robot to a position indicated by the navigation software;

a target robot position, or at least a suitable robot position is determined;

in this case the user may block the passive structure such that it will be rigidly held in place;

when the screw trajectory is inside the robot's workspace the robot starts to automatically follow it in real-time i.e. the vertebrae and the robot positions are measured and if one of them moves the robot will change the position of the tool to compensate;

the user can proceed with the desired surgical procedure.

In an embodiment, the invention concerns a method for assisting a user for removing volumes in the body of a patient using a robot attached to a passive structure and holding a tool, wherein said method comprises the following steps:

after a marker of the tracking system is attached to the patient the patient' position is registered in that the transformation between the position of the volumes and of the attached marker is found;

the robot is positioned such that the planned volume(s) to be removed is (are) inside the robot's workspace by moving the passive structure;

a navigation software assists the user in doing this task, whereby the user unblocks the passive structure and manually moves the robot to the position indicated by the navigation software;

a target robot position, or at least suitable, robot position is determined;

in this case the user may block the passive structure such that the robot will be rigidly held in place;

when the volume(s) to be removed is (are) are in the robot's workspace the robot starts to automatically compensate for the patient movements in real-time i.e. marker and the robot positions are measured and if one of them moves the robot will change the position of the tool to compensate;

the user can proceed with the standard surgical procedure whereby the navigation software controls the robot's position so that the tool held by the robot (driller or shaver) does not violate the "no-go" zones defined during planning.

In an embodiment, the methods comprise a haptic interaction of the surgeon with the device.

In an embodiment the user feels repulsive/wall-like forces on the haptic device when the tool approaches the "no-go" zone.

In an embodiment the volumes to be removed (stay-in zones) and volumes that must be protected (no-go zones) are defined preoperatively or intra-operatively.

In an embodiment if the user wants to remove certain volumes he enters it with the tool and inside said volume the tool remains blocked inside until he explicitly wants to leave it ("stay-in" volume).

In an embodiment when the tool stays inside the stay-in volume the user feels repulsive/wall-like forces that prevent him from leaving the volume.

In an embodiment margins of interaction around the "no-go" and "stay-in" zones can be defined.

In an embodiment the coupling between the haptic device movements and the robot movements is definable to allow the user to have small movements/high precision or big movements/high speed.

In an embodiment automatic compensation of the patient's movement is switched off and is done manually by the user.

In an embodiment the target position of the robot or at least a suitable robot position is determined as a semi-transparent phantom image (indicator) on a screen, and the phantom is in a first color at the beginning and changes to another color when the robot's workspace contains the screw trajectory or when the robot's workspace contains the volume to be removed. Other indicators may be used.

In an embodiment the invention concerns a device comprising at least a surgery planning software,
a robotic system, comprising an active robot and a passive structure for positioning the active robot and a controller,
a measurement system for real-time patient and robot position measurements and position tracking, and
a workstation with a navigation software controlling the device and for providing feedback to the user.

In an embodiment the workstation is a computer, such as a personal computer.

In an embodiment a computer contains the surgery planning software and monitors the measurement system.

In an embodiment the active robot covers a small volume and the passive structure covers a large volume.

DETAILED DESCRIPTION OF THE INVENTION

Spine Surgery

The robotic system described in this part is used to assist the surgeon while placing the screws into a vertebrae, as a practical example. The system comprises the following elements (see also FIG. 7):

1. A surgery planning software (known in principle in the art)
  a) the planning is based on medical images obtained pre-operatively (CT, MRI or other methods)
  b) the planning software allows the surgeon to define needed data for the surgery which can be: screw trajectories and data for the registration. The planning software can suggest the surgeon the best trajectories for the screws
  c) if the point to point followed by the surface matching registration method is used the surgeon defines landmarks (natural or artificial) and generates a 3D model of the vertebrae Alternatively, it is possible to use the following system without the explicit pre-operative planning. In such case, the user/surgeon inter-operatively decides about the trajectory based on his experience and/or medical images.

2. Compact robot with sufficient accuracy and rigidity. The corresponding robotic system is disclosed in parallel applications EP N.degree. 11160893.1 filed on Apr. 1, 2011 and PCT application N.degree.PCT/IB2012/051607, filed on Apr. 2, 2012, both in the name of the same Applicant as the present application and the content of which is incorporated by reference in its entirety in the present application.
  a) the robot positions or helps to position surgical tools
  b) the robot has sufficient number of degrees of freedom to define the screw trajectories in space,
  c) the robot's absolute accuracy should be the same or better than the accuracy provided by the optical tracking, medical imaging and application requirements. For example, this accuracy could be around 0.1 mm.
  d) the robot's rigidity should be sufficient to ensure the robot's accuracy while the surgeon operates the tools, the robot's workspace should be big enough so that manual positioning of the robot (using the passive structure) is simple, 3. Robot's controller (see the robotic system disclosed in applications EP N.degree.11160893.1 filed on Apr. 1, 2011 and PCT application N.degree.PCT/IB2012/051607 filed on Apr. 2, 2012 mentioned above)
  a) controls the robot's end effector position and/or velocity and/or force,
  b) can have different control modes: position, velocity, torque.

4. Passive structure positioning the robot in space (see the robotic system disclosed in applications EP N.degree.11160893.1 filed on Apr. 1, 2011 PCT application N.degree.PCT/IB2012/051607 filed on Apr. 2, 2012 mentioned above),
  a) the passive structure can be in a blocked state holding the robot rigidly in space or in an unblocked state allowing the surgeon to freely position (manually by the surgeon) the robot in space,
  b) the passive structure extends the robot's workspace and should be designed so that all required tool positions can be achieved,
  c) the passive structure's rigidity should be sufficient so that the system composed of the passive structure and the robot has the required accuracy while the surgeon operates the tools,
  d) it should be possible to integrate the passive structure with the equipment in the operating room
  e) to simplify the usage of the passive structure it can have additional features like: a gravity compensation, a manipulation adapted to one person, a feasible blocking/unblocking interface (ex. pedals)

5. Measurement system for real-time patient and robot position measurements (see the robotic system disclosed in applications EP N.degree.11160893.1 filed on Apr. 1, 2011 and PCT application N.degree.PCT/IB2012/051607 filed on Apr. 2, 2012 mentioned above)
  a) different measurement systems can be used known in principle in the art: electromagnetic, fixed (when target bone/tissue position is fixed and robot arm is used to register it), template-based and others. The most popular is an optical tracking, with appropriate markers.
  b) the optical tracking system comprises for example a camera, markers (attached to the robot and the patient) and a pointer (which can measure a single point in space),
  c) precision of the optical tracking system should be sufficient to fulfill the system requirements. For example it should be around 0.2 mm.
  d) if the robot's position real-time update (explained later) is to be used the frequency of the measurements (for the whole scene, not one marker) should be sufficient to avoid delays, for example around 20 Hz.
  e) the tool position (held by the robot or surgeon) can be also measured. In this case measuring the robot's position could not be necessary 6. Workstation with navigation software controlling all devices and providing feedback for the surgeon (see FIGS. 2(*a*)-2(*b*), 3(*a*)-3(*b*)).
  a) the navigation software knows about the patient and robot positions. It can measure the tool position (if relevant), b) the navigation software can help the surgeon to find offset between the patient's marker and the vertebrae in the registration process, c) the navigation software can command the robot's position, d) the navigation software controls the robot's position so that the surgeon with the robotic assistance places the screw along the planned trajectory, e) the robot's controller can be external or integrated in the navigation software, f) the navigation software can assist the surgeon in going through phases of the surgery, g) the navigation software can present to the surgeon a graphical feedback: real-time 3D rendering of the measured objects (robot, patient, pointer) and medical images h) the navigation software can integrate interface to the equipment of the operating room like C-Arm, O-Arm. Especially in case of integration with intra-operative medical imaging these devices can provide automatic registration processes and support surgical planning.

i) the navigation software can use different input devices: touchscreen, touchpad, mouse, keyboard, pedals and specialized input devices.

The navigation software may be used to allow the robot to follow any movement of the patient whereby the position is changed. This function may be automatic or on demand. from different devices (MRI, fluoroscopy, scanners, ultra sound). The CT images must have proper resolution which can be achieved using standard scanners. The surgeon using standard surgical views (Axial, Sagittal, Coronal) and a 3D view defines screw trajectories, natural landmarks (for a point to point registration) and generates 3D model of the vertebrae (for a surface matching and visualization). Data is saved to the file which can be read by the navigation software.

Alternatively, the planning can be done intra-operatively when the user/surgeon defines the trajectories using elements of the system (like pointer or trocar) and saves them for future execution.

Figure 2A:
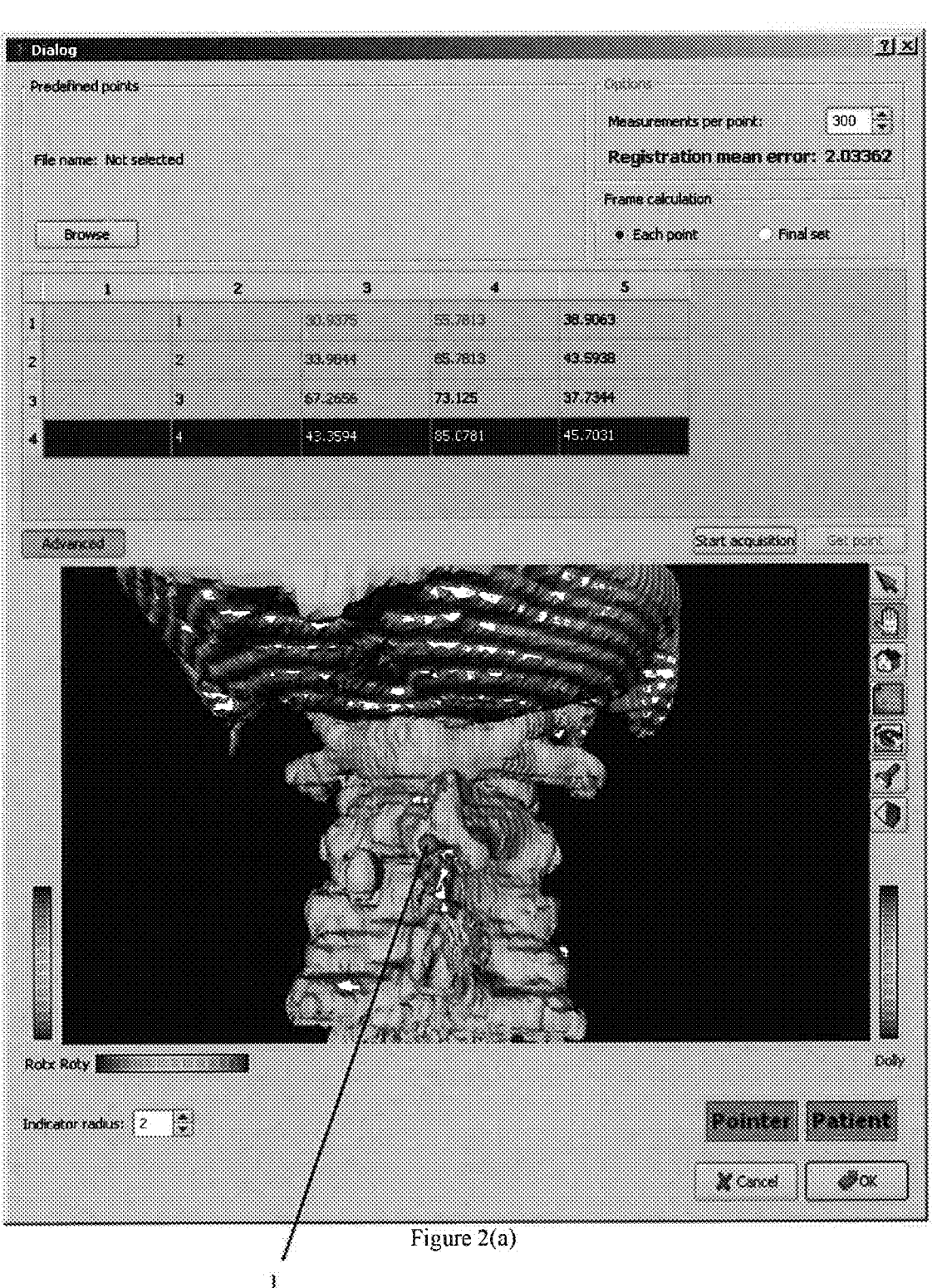
Figure 2B:
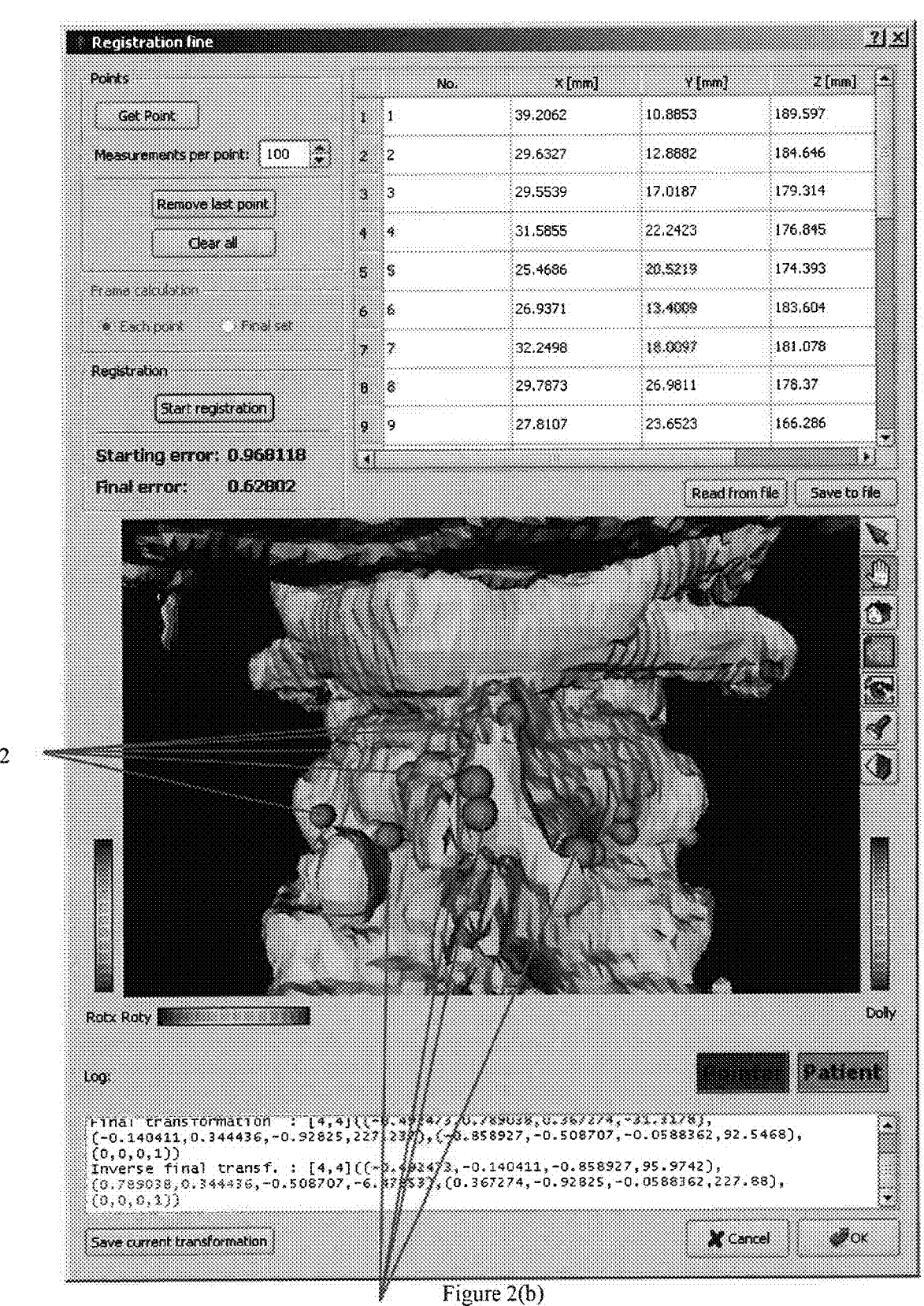

FIG. 2 illustrates the dialogs (screenshots) used during the patient registration typically as presented on the screen of a workstation: specifically, FIG. 2(a) illustrates point to point registration (coarse registration), and FIG. 2(b) illustrates surface matching (fine registration)

During the surgery the patient lies prone with his head fixed in the Mayfield structure M (see FIG. 1). When access to the vertebrae is open, an optical marker of the optical tracking system is attached to it.

Alternatively, patient registration can be done automatically using an intra-operative imaging device.

In the next step the patient's position is registered (the transformation between the vertebrae and attached marker and/or planning is found). Such procedures are known in principle in the art.

Firstly (as a coarse registration) the user/surgeon measures natural landmarks on the vertebrae (using a pointer for example), the same as defined during the planning on images obtained pre-operatively. A navigation software assists him in doing that by showing the natural landmarks on the 3D model (ref FIG. 2a). Specifically, FIG. 2(a) shows a 3D model of the vertebrae (medical images can be used too) with a landmark to be measured shown with a sphere 1. A list of points to be measured is available. User/Surgeon is informed if markers of the optical tracking system are occluded and/or if the precision of the measurement is decreased. A specialized algorithm may be used to find best matching between measured and planned points. The error is shown to the user and if it is sufficiently small the user can proceed to the next step.

The software finds the best correspondence between the set of planned and measured points and shows an estimated error to the surgeon. If the error is acceptable the surgeon can start measuring random points on a surface of the vertebrae (fine registration). When a sufficient number of points is collected (for example 30 points) the navigation software will look for the best match between them and the 3D model of the vertebrae generated during the planning. When the best match is found, the results with an estimated error are shown (ref FIG. 2b). If the error is acceptable the surgery can progress to the next stage, otherwise the registration should be restarted. Specifically, FIG. 2(b) shows the situation where multiple points (illustrated as spheres 2) on the surface of the vertebrae were measured and are added to the 3D model of the vertebrae (medical images can be used too). A list of already measured points is available. The user/surgeon is informed if markers of the optical tracking system are occluded and/or if the precision of the measurement is decreased. Registration is started when a sufficient number of random points is measured and a calculated error is shown to the user.

In the next step the robot R should be positioned using the passive structure PS so that the planned screw trajectory is inside the robot's workspace. The navigation software assists the user/surgeon in doing this task. The user/surgeon unblocks the passive structure and manually moves the robot to the position indicated by the navigation software. The ideal robot position can be shown for example as a semi-transparent phantom (indicator). The phantom is in one color (for example red) at the beginning and changes to another color (for example green) if and when the screw trajectory is inside the robot's workspace. In this case the surgeon can block the passive structure which will rigidly hold the robot in place for the procedure. Of course, other means and procedure can be used to position the robot, for example using haptic principles to indicate to the user when the trajectory is within the working volume. Also other equivalent indicators may be used to position the robot in the proper working volume for the intended procedure.

Figure 3A:
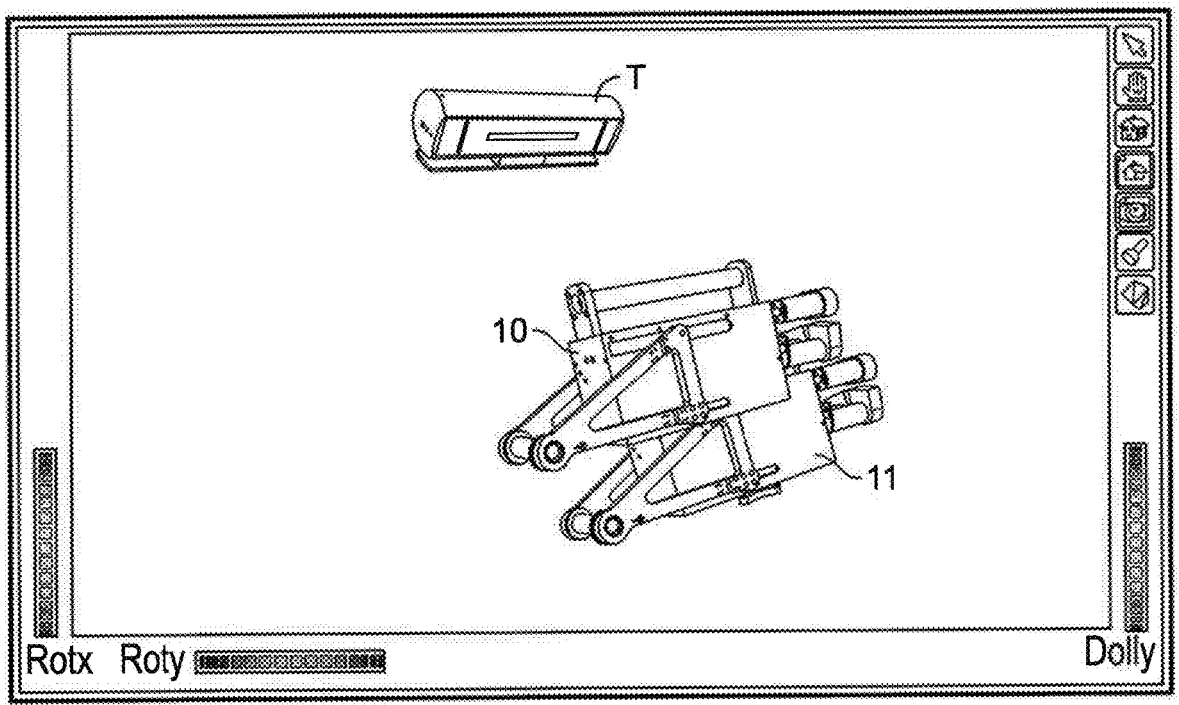
Figure 3B:
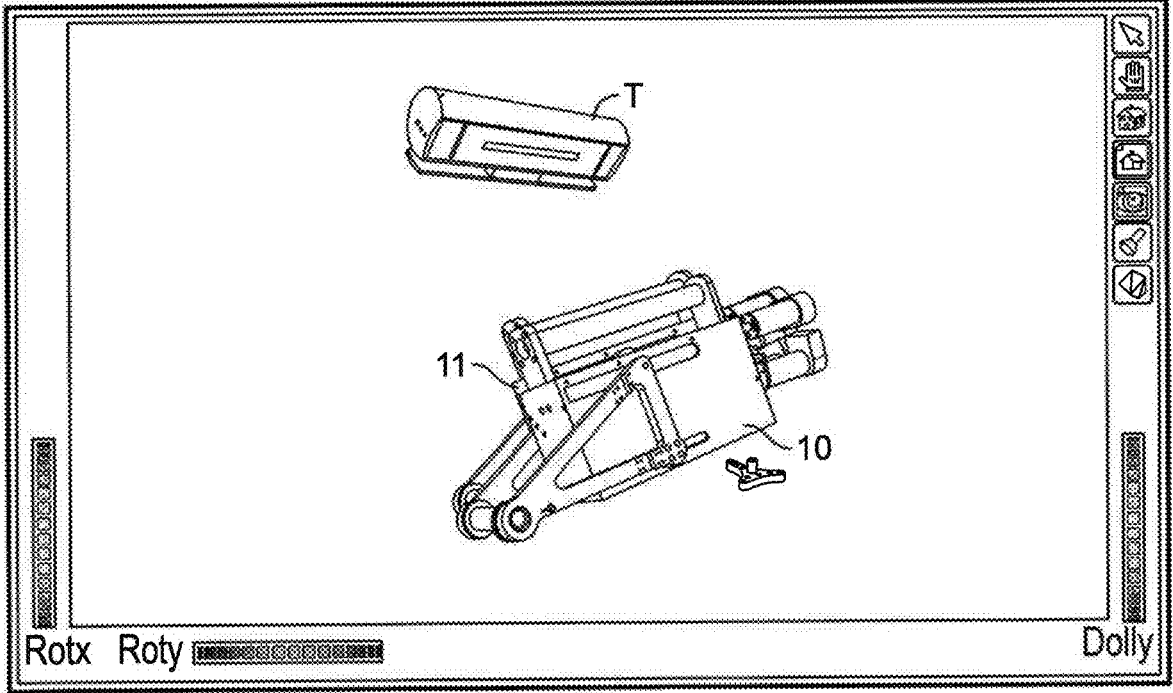

FIG. 3 illustrates exemplary indicators helping the user/surgeon to manually position the robot R after unblocking the passive structure PS. The current robot position 10 is shown for example in grey, the ideal robot position is shown for example as a semi-transparent color indicator, reference 11. If the planned screw trajectory is outside the robot's workspace the indicator is in one color for example red FIG. 3(a), otherwise it takes another color, for example green FIG. 3(b) when the screw trajectory is in the in the working volume.

When the screw trajectory is inside the robot's workspace the robot can start to automatically follow it in real-time i.e. the vertebrae and the robot positions are measured and if of one of them moves the robot will change the position of the tool to compensate. This is an important feature that increases precision, decreases forces exceeded on the vertebrae and is not possible to do manually. This is done by tracking a change of the position of a vertebrae and imposing the same change to the robot. Alternatively, this function may not be automatic but only upon request by the user.

Now the user/surgeon can proceed with the standard surgical procedure which comprises a drilling (using sharpened wire called K-wire), optionally drilling using a cannulated drill and a screw placement.

Different procedures can of course be used with other systems (e.g. non-cannulated systems).

Figure 5:
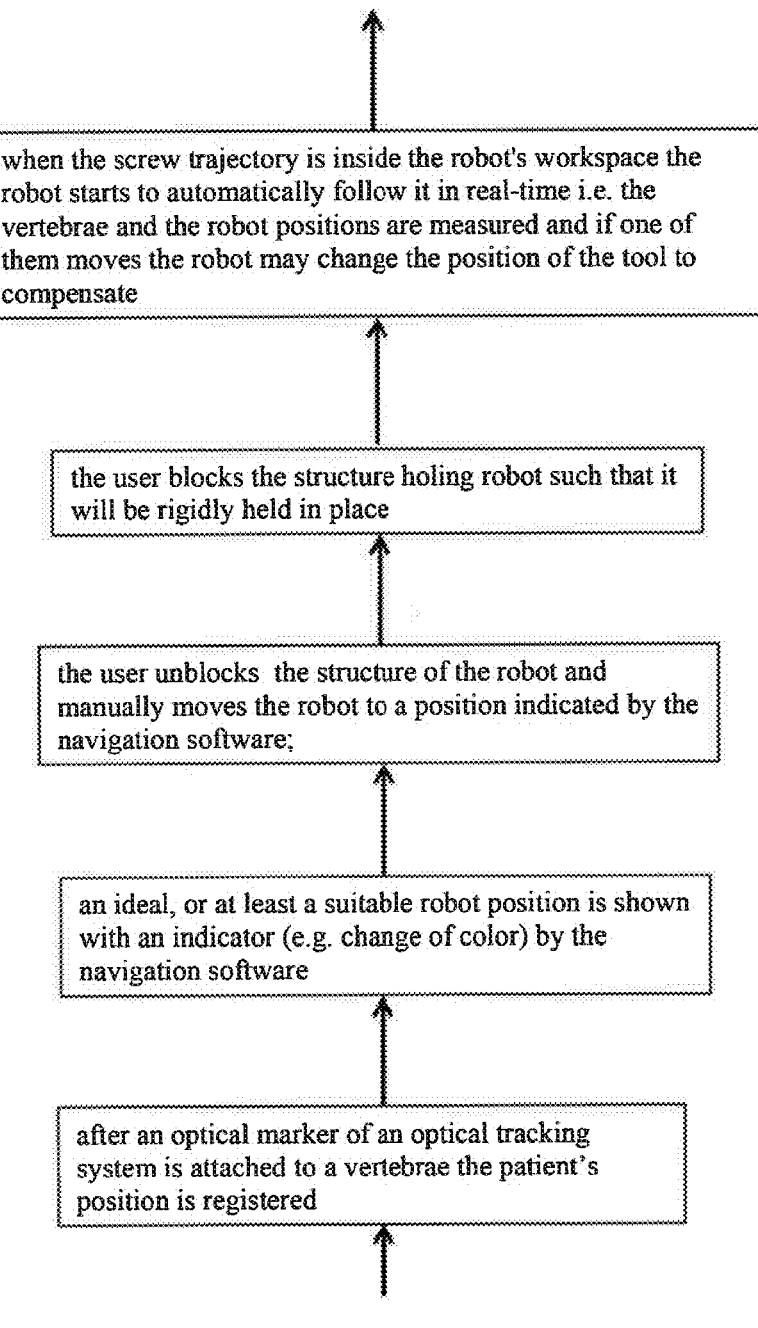
FIG. 5 illustrates a block diagram of the method in one embodiment.

FIG. 5 illustrates an example of an embodiment of the method with a block diagram comprising the general steps.

All operations are done through a tube held by the robot (called trocar) which ensures that the screw is placed in the position defined by the robot. After the screw is placed the surgeon can place another screw in the same vertebrae or move to another vertebrae and redo the process.

Different procedures can be applied for percutaneous surgeries.

ENT Surgeries

BACKGROUND

Some of the ENT (Ear Nose Throat) surgeries comprise the step of removing volumes like tumors, polyps etc. Users/Surgeons use drillers (for bones) and shavers (for soft tissues) which they operate manually. Different tools for tissue removal can be used like lasers, coagulators etc. In many cases they use an endoscopic camera which is not convenient because of a bleeding which drastically decreases the field of view. When the bleeding begins the user/surgeon has to stop the operations, put on a dressing and wait until it stops. For this reason the ENT surgeries take a lot of time. They can be dangerous because when the visibility is constrained important tissues like nerves, orbitals, brain etc. can be destroyed by accident.

System Elements

System elements are similar to the ones used in the spinal surgeries (see above and FIG. 7) with the following changes:
1. Planning:
   b) instead of the screw trajectories the user/surgeon defines volumes that he wants to remove (called "stay-in" zones like tumors, polyps) and volumes that must be protected (called "no-go" zones like nerves, orbitals and other important tissues)
2. Compact robot (see the robotic system disclosed in applications EP N.degree.11160893.1 filed on Apr. 1, 2011 and PCT application N.degree.PCT/IB2012/051607 filed on Apr. 2, 2012 mentioned above)
   b) the robot has sufficient number of degrees of freedom to guide the driller or shaver or another surgical tool in space, for example 5 or 6 DOFs.

Additional Points:
   the robot may have force sensor(s) integrated,
   the force sensor(s) may be mounted on the tool tip (for measuring forces on the tool tip) and/or in the tool fixation (for measuring forces on the tool)
1. Robot's controller:
   b) should have control mode suitable for teleoperation
2. Workstation with navigation software ( . . . ):
   d) the navigation software controls the robot's position so that the tool held by the robot (driller or shaver) does not violate the "no-go" zones defined during planning. If the user/surgeon wants to remove certain volumes he should enter it with the tool. Inside such volumes the tool remains blocked inside until he explicitly wants to leave it ("stay-in" zone). There are other way of realizing the concept of "stay-in" and "no-go" zones the idea being to make such procedures safer.

Additional Points:
   the user/surgeon commands the robot positions using a haptic device, the principle of such devices being known in the art when the tool approaches the "no-go"

zone the user/surgeon feels repulsive/wall-like forces on the haptic device to inform him of the position of the tool when the tool is supposed to stay inside the stay-in volume the user/surgeon feels repulsive/wall-like forces that prevent him from leaving the volume as long as it is required the margin of interaction around the "no-go" and "stay-in" zones may be defined, the coupling between the haptic device movements and the robot movements may be defined to allow the surgeon to have small movements/high precision or big movements/high speed and additional features like tumor removal.

Surgery Workflow (See FIG. 6)

Planning is similar as in the system used for the spinal surgery. Instead of the screw trajectories surgeon should generate models for the "no-go" and "stay-in" zones in the preoperative images. Alternatively, such zones may be defined during the procedure if this is possible or suitable.

Registration and manual robot positioning using passive structure is the same as for the spinal surgery disclosed above.

The tool used in the surgery (for example driller, shaver) should be fixed to the robot R end effector. When desired volumes are inside the robot's workspace the user/surgeon can control the robot position using the haptic device with the assistance of the navigation software.

When approaching a "no-go" zone the user/surgeon a feels repulsive force on the haptic device which prevents him from touching important tissues.

When he enters a "stay-in" zone he remains blocked inside said zone until he explicitly wants to leave. He can move the tool inside the volume and follow for example virtual tumor walls felt on the haptic device until he is sure to remove all needed tissue. The margins of interaction with walls can be defined so for example it is possible to remove 80% of the tumor or 120% (tumor and tissues around). The coupling between the haptic device and the robot movements can be defined so that the surgeon can have small movements/high precision or big movements/high speed. Other algorithms for controlling the haptic device can be implemented.

High bleeding can be accepted as it does not disturb the robot operation (the robot and patient positions are measured by the optical tracking so there is no need for endoscope except from control and verification). As tumor can be removed fast (in few minutes) high bleeding during a short time for patient can be accepted.

Figure 4:
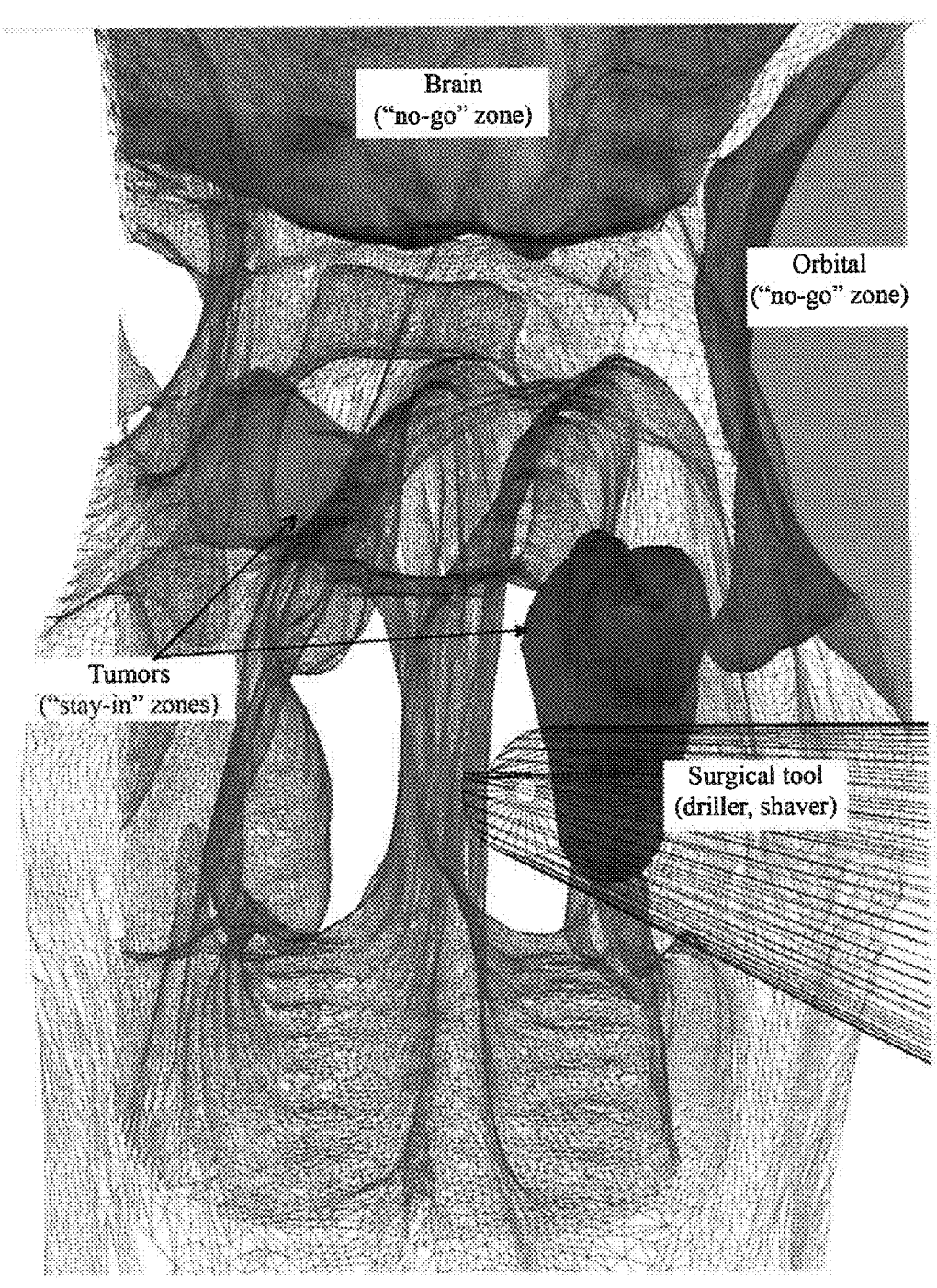
FIG. 4 illustrate a screenshot of an ENT surgical procedure.

FIG. 4 illustrates screenshots of the navigation software used in the ENT surgery. The surgeon controls the tool position using a haptic device. He can feel repulsive forces when he approaches the "no-go zones" and he can stay inside the "stay-in zone" until he is sure to remove all needed tissue.

FIG. 6 illustrates an example of an embodiment of the method with a block diagram comprising the general steps.

Figure 7:
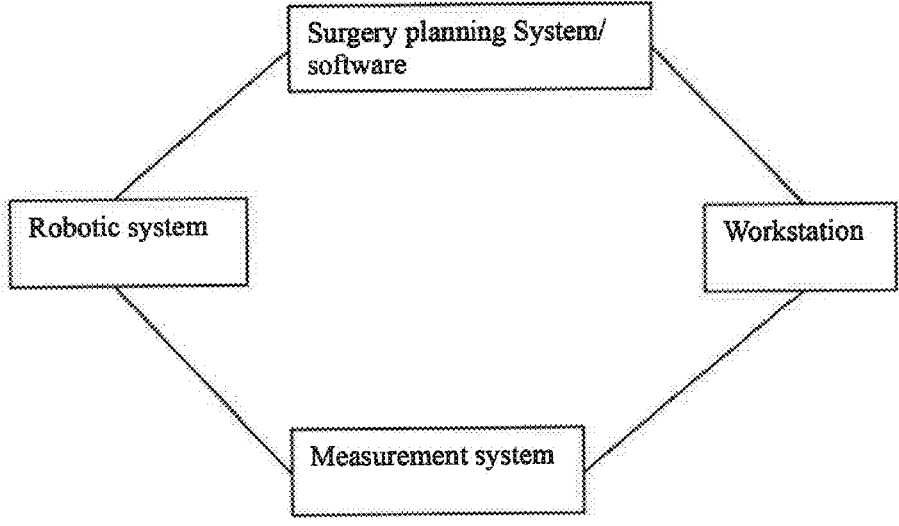
FIG. 7 illustrates a block diagram of the system according to the invention.

FIG. 7 illustrates in block-diagram an example of a system of the invention with the different elements forming a system suitable for carrying out the method. As defined hereabove, the system comprises at least a surgery and planning system, a robotic system, a measurement system and a workstation, such as a computer station.

The examples and values (sizes, DOF etc) given in the above description are only for illustrative purposes and should not be construed in a limiting manner on the scope of the invention. Also, equivalent means may be envisaged by a skilled person and the embodiments described herein may also be combined as desired.

The invention claimed is:

1. A robotic surgical system for assisting a surgeon in preparing a hole in a spine of a patient and placing a screw in the hole during an operation, the system comprising:
   a robot comprising an end-effector for holding a surgical tool for use in drilling the hole and placing the screw in a vertebra of the patient;
   a controller for controlling the position of the end-effector, wherein the end-effector can be manually and freely positioned by the surgeon during the operation; and
   a measurement system with a computer processor for:
      measuring a position of the surgical tool held by the end effector and a position of the vertebra of the patient;
      determining a change in the position of the vertebra; and
      automatically adjusting the position of the end effector holding the surgical tool based at least in part on a change in the position of the vertebra to maintain a planned screw trajectory such that a spatial relationship between the end effector and the vertebra defined by the planned screw trajectory remains substantially unaltered as the operation is performed, thereby ensuring the surgical tool remains aligned with the planned screw trajectory as a hole in the vertebra is prepared and a screw is placed in the hole,
   wherein the computer processor is configured to store a location of a volume to be protected, wherein a no-go zone is defined based at least in part on the volume to protect from removal,
   wherein the processor is configured to control a position of the robot such that the surgical tool does not enter the volume to be protected.

2. The robotic surgical system of claim 1, wherein the computer processor is configured to store a location of a target volume to protect from removal, wherein a stay-in zone is defined based at least in part on the target volume.

3. The robotic surgical system of claim 2, wherein the processor is configured to control a position of the robot such that the surgical tool enters the target volume and remains in the stay-in zone.

4. The robotic surgical system of claim 3, wherein based on a position of the tool in the target volume, a repulsive/wall-like force is provided to a surgeon manipulating the surgical tool to inform the surgeon of the position of the surgical tool inside the stay-in zone.

5. The robotic surgical system of claim 3, wherein the processor is configured to prevent removal of a portion of the surgical tool from the target volume thereby keeping the portion of the surgical tool within the target volume until the surgeon explicitly wants to leave the target volume.

6. The robotic surgical system of claim 3, wherein the target volume and the volume to be protected from removal are defined preoperatively.

7. The robotic surgical system of claim 2, wherein the target volume and the volume to be protected are defined intra-operatively.

8. The robotic surgical system of claim 1, wherein based on a position of the tool outside the no-go zone, a repulsive/wall-like force is provided to a surgeon manipulating the surgical tool to inform the surgeon of the position of the surgical tool outside the no-go zone.

9. The robotic surgical system of claim 1, wherein the surgical tool is a drill.

10. The robotic surgical system of claim 1, wherein the processor is configured to adjust the position of the surgical tool based at least in part upon a position of a haptic device controlled by a surgeon.

11. The robotic surgical system of claim 10, wherein a coupling between the position of the haptic device and the position of the surgical tool is definable such that a user may make small movements with high precision or large movements with high speed.

12. The system of claim 1, wherein the robot allows positioning of the surgical tool by a surgeon with at least four degrees of freedom.

13. The system of claim 1, wherein the position of the vertebra is a position of a marker placed in spatial relation to the vertebra.

14. The system of claim 1, wherein the measurement system is an optical tracking system comprising a camera, an electro-magnetic tracking system, fixed measurement system, or template-based tracking system.

15. The system of claim 14, wherein the measurement system comprises a first marker attached to the robotic surgical system and a second marker attached to the patient.

16. The system of claim 1, comprising a force sensor for measuring forces on the surgical tool.

17. The system of claim 16, wherein the force sensor is mounted on the end-effector.

18. The system of claim 1, wherein the robotic surgical system comprises a display for providing graphical feedback to a surgeon.

19. The system of claim 1, wherein the surgical tool is a tube.

20. The system of claim 1, further comprising:
   a passive structure directly coupled to the robot and rigidly holding the robot in place; and
   a camera, configured to optically track the robot and the patient, directly coupled to the passive structure.

* * * * *